(12) United States Patent
Sas et al.

(10) Patent No.: US 7,842,719 B2
(45) Date of Patent: Nov. 30, 2010

(54) USE OF ENDOPEROXIDES FOR THE TREATMENT OF INFECTIONS CAUSED BY FLAVIVIRIDAE, INCLUDING HEPATITIS C, BOVINE VIRAL DIARRHEA AND CLASSICAL SWINE FEVER VIRUS

(75) Inventors: Benedikt Sas, Stekene (BE); Johan Van hemel, Antwerp (BE); Jan Vandenkerckhove, Zichem (BE); Eric Peys, Balen (BE); Johan Neyts, Kessel Lo (BE)

(73) Assignee: Kemin Foods, L.C., Des Moines, IA (US)

( * ) Notice: Subject to any disclaimer, the term of this patent is extended or adjusted under 35 U.S.C. 154(b) by 877 days.

(21) Appl. No.: 10/664,008

(22) Filed: Sep. 16, 2003

(65) Prior Publication Data

US 2005/0059647 A1     Mar. 17, 2005

Related U.S. Application Data

(60) Provisional application No. 60/422,683, filed on Oct. 31, 2002.

(51) Int. Cl.
  *A61K 31/335*  (2006.01)
  *A61K 38/00*  (2006.01)

(52) U.S. Cl. .......................... 514/450; 514/2

(58) Field of Classification Search ............. 514/450
  See application file for complete search history.

(56) References Cited

U.S. PATENT DOCUMENTS

| | | | |
|---|---|---|---|
| 5,677,331 A | 10/1997 | Zhou | |
| 5,725,859 A | 3/1998 | Omer | |
| 2007/0142459 A1* | 6/2007 | Schlegel et al. | 514/452 |

FOREIGN PATENT DOCUMENTS

| | | | |
|---|---|---|---|
| CN | 1122806 A | * | 5/1996 |
| DE | 19902924 | | 8/2000 |
| EP | 0 456 149 A1 | | 11/1991 |
| EP | 0 713 877 A1 | | 5/1996 |
| JP | H4-225983 A | | 8/1992 |
| WO | PCT/CN01/00884 | | 5/2001 |

(Continued)

OTHER PUBLICATIONS

Qian et al. "the immunologic and antiviral effect of Qinghaosu," Journal of Traditional Chinese Medicine, 1982, vol. 2, No. 4, pp. 271-276.*

(Continued)

*Primary Examiner*—Shengjun Wang
(74) *Attorney, Agent, or Firm*—Kent A. Herink; Emily E. Harris

(57) ABSTRACT

The use of sesquiterpenes and, in particular sesquiterpene lactone endoperoxides, such as artemisinin and analogs thereof, for the treatment of hepatitis C virus infections. Artemisinin, analogs of artemsisnin and some crude *Artemisia* extracts were tested in vitro against DNA-viruses, retro-viruses and *Flavivirida*, (an important family of human and animal RNA pathogens). These compounds were also screened for anti-tumor activity. Strong activity of artemisinin was noticed against the bovine viral diarrhea virus (BVDV). As pestiviruses, such as BVDV, share many similarities with hepatitis C virus (HCV), we can conclude that endoperoxides in general and artemisinin more specifically have efficacy as treatments for hepatitis C viral infections.

3 Claims, 1 Drawing Sheet

Artemisinin

Dihydroartemisinin

Artesunate

Artemether

FOREIGN PATENT DOCUMENTS

WO    PCT/JP01/09199    10/2001

OTHER PUBLICATIONS

Zheng et al, Chemical Abstracts on STN, Abstract No. 119CA:173663, Oct. 30, 1993, "Experimental study of inhibitory effect of four traditional Chinese herb medicines on epidemic hemorragic fever virus", Hunan Yike Daxus Xuebao, vol. 18 (2), pp. 165-167, 1993.

Efferth, T., "Antiviral activity of artesunate towards wild-type, recombinant and ganciclovir-resistant human cytomegaloviruses", J. Mol. Med., 2002, pp. 233-242.

Zheng et al., Experimental study of inhibitory effect of the four traditional Chinese herb medicines on epidemic hemorrhagic fever virus, Chemical Abstracts, 1993, vol. 119, 119:173663x.

Jung, M. et al, Synthesis and in vitro anti-human immunodeficiency virus activity of artemisinin (qinghaosu)-related trioxanes, Bioorganic & Medicinal Chemistry letters, 1994, vol. 4, No. 7, pp. 931-934.

Hyoujyunn Biseibutsu-gaku (Standard Microbiology), 1997, 6th edition, pp. 424-426, pp. 461-463.

* cited by examiner

USE OF ENDOPEROXIDES FOR THE TREATMENT OF INFECTIONS CAUSED BY FLAVIVIRIDAE, INCLUDING HEPATITIS C, BOVINE VIRAL DIARRHEA AND CLASSICAL SWINE FEVER VIRUS

This application claims priority to U.S. patent application Ser. No. 60/422,683 filed Oct. 31, 2002.

BACKGROUND OF THE INVENTION

The invention relates generally to the use of sesquiterpene lactones in the treatment of infections caused by *Flaviviridae* and, more specifically, to the use of sesquiterpene lactone endoperoxides to treat hepatitis C infections, yellow fever, dengue fever, bovine viral diarrhea and classical swine fever.

Chronic hepatitis C infection is a substantial public health problem affecting 180 million people worldwide (3% of the population), including 4 million people in the United States and is a leading cause of chronic liver disease. It is predicted that HCV infection will continue to rise in the U.S. with three times as many people infected by the year 2010. Infection with the hepatitis C virus may lead to an increased probability of developing serious and, in some cases, life threatening chronic liver disease including liver failure and cancer.

Chronic liver disease is the tenth leading cause of death among adults in the United States, and accounts for approximately 25,000 deaths annually, or approximately 1% of all deaths. Population-based studies indicate that 40% of chronic liver disease is HCV-related, resulting in an estimated 8,000-10,000 deaths each year. Current estimates of medical and work-loss costs of HCV-related acute and chronic liver disease are greater than $600 million annually, and HCV-associated end-stage liver disease is the most frequent indication for liver transplantation among adults. Because most HCV-infected persons are aged 30-49 years, the number of deaths attributable to HCV-related chronic liver disease could increase substantially during the next 10-20 years as this group of infected people reaches ages at which complications from chronic liver disease typically occur.

HCV is transmitted primarily through large or repeated direct percutaneous exposures to blood. In the United States, the two most common exposures associated with transmission of HCV are blood transfusion and injecting-drug use. Therapy for hepatitis C is a rapidly changing area of clinical practice. Combination therapy with interferon and ribavirin, a nucleoside analogue, is approved for the naive treatment of patients with chronic hepatitis C. Studies of patients treated with a combination of ribavirin and interferon have demonstrated a substantial increase in sustained response rates, reaching 40%-50%, compared with response rates of 15%-25% with interferon alone. Most patients receiving interferon experience flu-like symptoms early in the treatment, but these symptoms diminish with continued treatment. Later side effects include fatigue, bone marrow suppression and neuropsychiatric effects (e.g. apathy, cognitive changes, irritability and depression). Interferon dosage must be reduced in 10%-40% of patients and discontinued in 5%-15% because of severe side effects. Ribavirin can induce hemolytic anemia and can be problematic for patients with pre-existing anemia, bone marrow suppression or renal failure. In these patients, combination therapy should be avoided or attempts should be made to correct the anemia. Hemolytic anemia caused by ribavirin also can be life-threatening for patients with ischemic heart disease or cerebral vascular disease. Ribavirin is teratogenic, and female patients should avoid becoming pregnant during therapy. Other treatments, including corticosteroids, ursodiol and thymosin, have not been effective. High iron levels in the liver might reduce the efficacy of interferon. Use of iron reduction therapy (phlebotomy or chelation) in combination with interferon has been studied, but results have been inconclusive (www.cdc.gov). Therefore, a strong medical need exists to discover and develop new bioactive molecules that can be used to treat hepatitis C infections with fewer or reduced side effects and better efficiency compared to the current available treatments.

SUMMARY OF THE INVENTION

It has been discovered that sesquiterpene lactones having the generic formula:

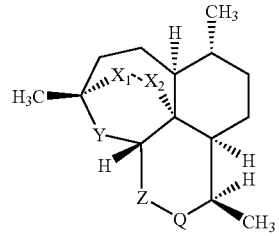

have activity against infections caused by *Flaviviridae*, including hepatitis C, bovine viral diarrhea, and classical swing fever viruses. Representative, presently preferred sesquiterpene lactones are described in this application, although it will be apparent to those skilled in the art that other sesquiterpene lactone compounds will be useful in the treatment of infections caused by *Flaviviridae*. Also included are pharmaceutically acceptable salts of these compounds.

Preferred sesquiterpene lactones are the sesquiterpene lactone endoperoxides artemisinin, dihydroartemisinin, artensunate, and artemether.

DETAILED DESCRIPTION OF PREFERRED EMBODIMENTS

Figure 1:
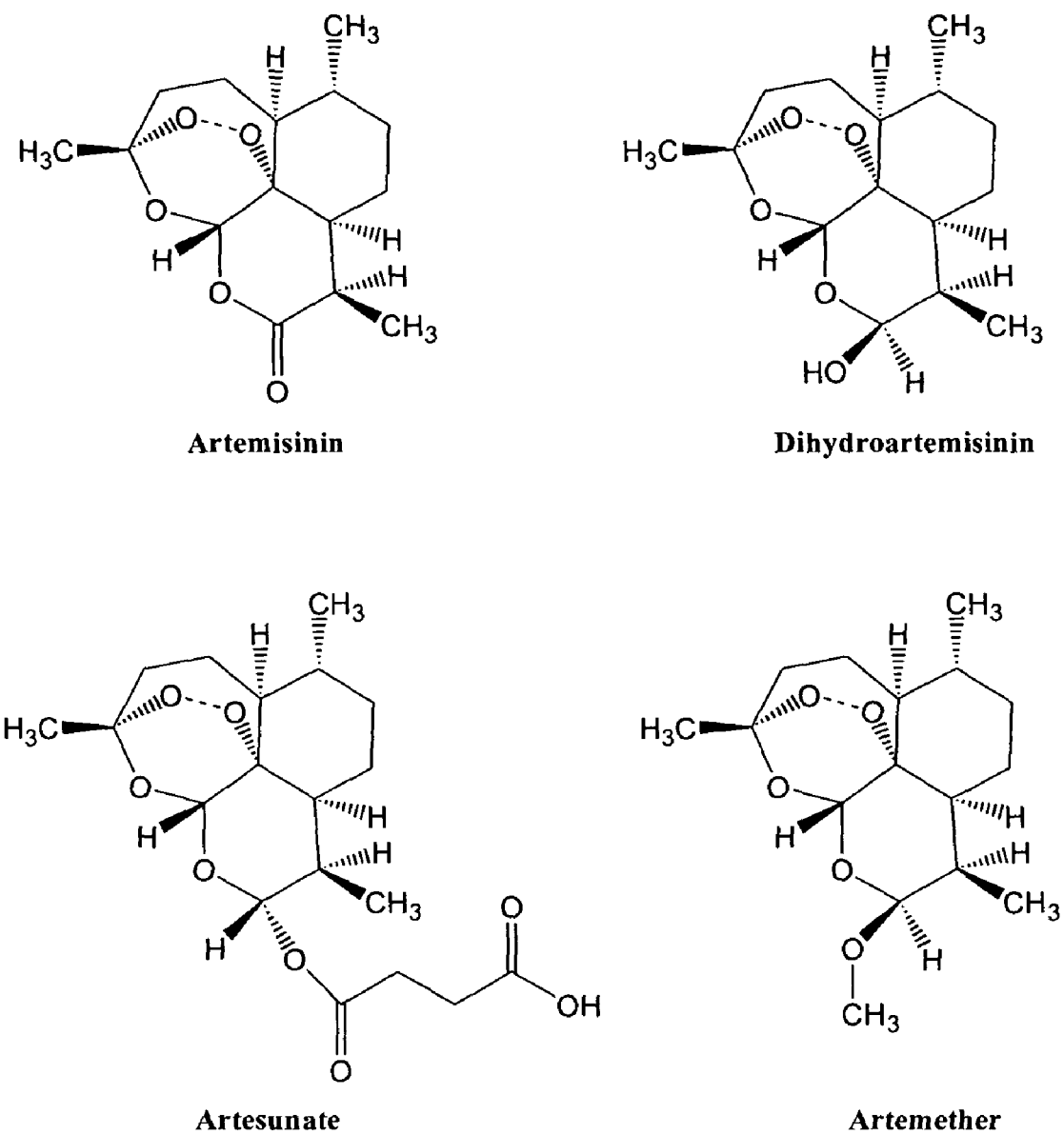
FIG. 1 is an illustration of the chemical structure of artemisinin, dihydroartemisinin, artemether and artesunate.

Here we describe the antiviral effect of sesquiterpene lactones, and preferentially sesquiterpene lactone endoperoxides, such as artemisinin, dihydroartemisinin, artemether and artesunate, against specific *Flaviviridae* such as the hepatitis C virus.

Preferred sesquiterpene compounds of the present comprise compounds of the formula:

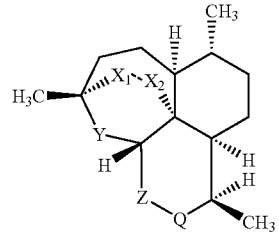

wherein: $X_1$ and $X_2$ are selected from O, S, Se and NH; Y is selected from O, S, Se, and NH; Z is selected from O, NH, S, and Se, and Q is selected from CO, CHOH, $CHOCH_3$, $CHOC_2H_5$, $CHOC_3H_7$, and $CHOCOCH_2CH_2COOH$, and the pharmaceutically acceptable salts thereof.

The presently particularly preferred sesquiterpene compounds of the invention include artemisinin, wherein $X_1$ and $X_2$ are O, Y is O, Z is O and Q is C=O; dihydroartemisinin (artemisinin except Q is CHOH), artemether (artemisinin except Q is $CHOCH_3$); arteether (artemisinin except Q is $COC_2H_5$); a propyl product (artemisinin except Q is CHOC$_3$H$_7$); and artesunate (artemisinin except Q is CHOCOCH$_2$CH$_2$COOH). The presently most particularly preferred sesquiterpene compound of the invention is dihydroartemisinin.

Endoperoxides have a peroxo linkage (—O—O—) that in these products is believed to be important to its activity as an antimalarial. Substitution of the peroxo linkage with a —S—S— (disulfide) or —Se—Se-(diselenide) or —N—O— or —NH—NH-(hydrazines) and the various combinations of these linkages will create novel compounds that also may have activity.

The *Flaviviridae* is an important family of human and animal RNA viral pathogens (Rice C M. 1996. *Flaviviridae: the viruses and their replication*. In: Fields B N, Knipe D M, Howley P M, eds. Fields virology. Philadelphia: Lippincott-Raven Publishers. Pp 931-960). The three currently recognised genera of the *Flaviviridae* exhibit distinct differences in transmission, host range and pathogenesis. Members of this classical flavivirus are the yellow fever virus, dengue virus and the pestiviruses, such as bovine viral diarrhea virus (BVDV) and the classical swine fever virus (CSFV). The most recently characterised member of this family is the common and exclusively human pathogen, hepatitis C virus (HCV). *Flaviviridae* are single strand RNA viruses having (+) sense RNA genome polarity. Other virus families with (+) sense RNA include the *Picornaviridae, Togaviridae, Caliciviridae* and the *Coronaviridae*.

The inventive compounds may be used in their native form or as salts. In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, acetate ascorbate, benzoate, citrate, etoglutarate, glycerophosphate, malonate, methanesulfonate, succinate, and tartarate. Suitable inorganic salts may also be formed, including bicarbonate, carbonate, hydrochloride, nitrate, and sulfate, salts.

Compounds of the present invention can conveniently be administered in a pharmaceutical composition containing the compound in combination with a suitable excipient, the composition being useful in combating viral infections. Depending on whether the preparation is used to treat internal or external viral infections, the compounds and compositions of the present invention can be administered parenterally, topically, intravaginally, orally, or rectally.

For parenteral administration, solutions of the active compound or its salts can be prepared in water, optionally mixed with a nontoxic surfactant. Dispersions can also be prepared in glycerol, liquid polyethylene glycols, triacetin, and mixtures thereof and in oils.

Useful dosages of the compound can be determined by comparing their in vitro activity. Methods for the extrapolation of effective dosages to humans are known to the art.

The compound is conveniently administered in unit dosage form; for example, containing 0.1 to 2000 mg, conveniently 100 to 1000 mg, most conveniently, 100 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

For internal infections, the compositions can be administered orally or parenterally at dose levels, calculated as the free base, of about 1 to 30 mg/kg, preferably 1 to 10 mg/kg of mammal body weight.

The exact regimen for administration of the compound and compositions disclosed herein will necessarily be dependent upon the needs of the individual subject being treated, the type of treatment and, of course, the judgment of the attending practitioner. The compounds of the present invention can be administered to an animal in need of treatment. In most instances, this will be a human being, but the treatment of livestock and companion animals is also specifically contemplated as falling within the scope of the instant invention.

Methods and Materials

Artemisinin was purchased from Aldrich. The crude plant extracts of wormwood (*Artemisia absinthum*) KE-4, sweet wormwood (*Artemisia annua*) KE-5, and tarragon (*Artemisia dracunculus*) KE-6, were obtained from Kemin Industries Inc., Des Moines, US. To prepare the KE-4, -5, and. -6 samples, 2 g of dried and grinded wormwood, sweet wormwood or tarragon, respectively, was stirred for 8 hours at room temperature with 200 ml of hexane p.a. Afterwards, the suspension was filtered through a G3 glass filter and evaporated under reduced pressure. The remaining dark residue was used for the biological screenings. Artemether, dihydroartemisinin and artesunate were purchased from Dafra Pharma. The compounds were screened against various pathogenic viruses such as the human immunodeficiency virus (HIV), herpes simplex virus (HSV), vaccinia virus (VV), the varicella zoster virus (VZV) and the human cytomegalovirus (CMV). For all viruses, except for CMV, the EC$_{50}$ (effective compound concentration required to inhibit HIV-induced cytopathicity in human CEM cell cultures, HSV-and VV-induced cytopathicity in human embryo fibroblast E$_6$SM cell cultures, and VZV-induced plaque formation in human embryonic lung (HEL) cell cultures by 50%.) was determined. For determination of antiviral activity, expressed in IC$_{50}$, against CMV, human embryonic lung fibroblast (HEL) cells grown in 96-well microplates were infected with 20 PFU virus/well.

After 2 hours of incubation at 37° C., the infected cells were replenished with 0.1 ml of medium containing serial dilutions of the test compound. On day 7 the plaques were counted microscopically after staining the cells with Giemsa's solution. The minimum antiviral concentration was expressed as the dose required to inhibit virus-induced plaque formation by 50%.

The compounds were also screened against *Flavivirida*. Due to the fact that there is no adequate in vitro analysis to screen against HCV, it was decided to screen against the bovine viral diarrhea virus (BVDV), as it shares many similarities with the hepatitis C virus (Frolov I, McBride S and Rice C M. *Cis-acting RNA elements required for replication of bovine.viral diarrhea virus-hepatitis C virus 5' non-translated region chimeras*. RNA 4, 1418-1435 (1998)). Further screenings of artemether against different strains of BVDV have been carried out.

The compounds were also checked for anti-tumor activity via the proliferation of murine leukemia cells (L1210/0), murine mammary carcinoma cells (FM3A) and human T-lymphocyte cells (Molt4/C8, CEM/0). The best antiviral activity observed against CMV and VZV was from KE 6. To a lesser extent, artemisinin showed antiviral activity against HSV-2 and VV.

Results and Discussion

In a first set of screenings (Table 1), the anti-viral activity of artemisinin and some crude *Artemisia* extracts (KE-4, KE-5 and KE-6) was checked against HIV-1, HIV-2, HSV-1, HSV-2, VV, CMV and VZV.

TABLE 1

Results of screenings against HIV-1, HIV-2, HSV-1, HSV-2, VV, CMV and VZV

| | $^a$EC50 (µg/ml) | | | | | | | | |
|---|---|---|---|---|---|---|---|---|---|
| Compound | HIV-1 (III$_B$) (CEM) | HIV-2 (ROD) (CEM) | HSV-1 (KOS) (E$_6$SM) | HSV-2 (G) (E$_6$SM) | VV (E$_6$SM) | CMV Davis (HEL) | CMV AD-169 (HEL) | VZV (HEL) OKA | VZV (HEL) YS |
| Artemisinin | >20 | >20 | >400 | 240 | 240 | >50 | >50 | >50 | >50 |
| KE-4 | >20 | >20 | >80 | >80 | >80 | >50 | >50 | >50 | >50 |
| KE-5 | >100 | >100 | >240 | >80 | >80 | >50 | >50 | >50 | >50 |
| KE-6 | >20 | >20 | >80 | >80 | >80 | 10 | 33 | 17 | 30 |

$^a$50% Effective concentration or compound concentration required to inhibit HIV-induced cytopathicity in human lymphocyte CEM cell cultures, HSV- and VV-induced cytopathicity in human embryo fibroblast E$_6$SM cell cultures, and CMV- and VZV-induced plaque formation in human embryonic lung HEL cell cultures by 50%.

A second anti-viral screening (Table 2) was performed in order to check the activity against bovine viral diarrhoea virus (BVDV-strain Pe515) in bovine kidney (MDBK) cells.

TABLE 2

Results of screenings against BVDV in MDBK cells

| Compound | EC$_{50}$ (µg/ml) BVDV | MTC (µg/ml) MDBK |
|---|---|---|
| Artensunate | 0.07 | 0.4 |
| Artemether | 0.3 | >100 |
| Artemisinin | 0.4 | >100 |
| Dihydroartemisinin | 0.05 | 0.4 |
| KE 4 | >100 | >100 |
| KE 5 | >100 | >100 |
| KE 6 | >100 | 100 |

Antiviral activity was assessed using the Pe515 strain of BVDV on MDBK cells. Both antiviral activity and cytotoxicity was determined by means of the MTS method. The EC$_{50}$ is the concentration required to reduce virus induced cytopathic effect by 50%. The MTC (minimal toxic concentration) was defined as the concentration that caused >=20% reduction in cell metabolism.

The MTC was not reached at the highest concentration (100 µg/ml) for MDBK cells when treated with artemether, artemisinin, KE 4 and KE5. In this test a strong activity of the endoperoxides artemisinin, dihydroartemisinin, artemether, and artesunate against BVDV, a *Flaviviridae*, was observed while the cell toxicity stayed low. Therefore, these products could be positioned as a possible treatment for infections caused by *Flaviviridae*.

Artemether was screened against different BVDV strains, as well as against BDV (border disease virus)(Table 3).

TABLE 3

Results of screening of artemether against BVDV and BDV

| Artemether | 100 µg/ml | 20 µg/ml | 4 µg/ml | 800 ng/ml | 160 ng/ml | 32 ng/ml | 6.4 ng/ml | 1.28 ng/ml | 0.512 ng/ml | 0.256 ng/ml |
|---|---|---|---|---|---|---|---|---|---|---|
| Non infected | Toxic | – | – | – | – | – | – | – | – | – |
| BVDV II ncp | Toxic | ++ | ++ | ++ | +++ | +++ | +++ | +++ | +++ | +++ |
| BVDV I cp | Toxic | + | + | + | + | ++ | ++ | ++ | ++ | ++ |
| BVDV I | Toxic | + | + | + | ++ | +++ | +++ | +++ | +++ | +++ |
| BDV | Toxic | + | + | + | ++ | ++ | ++ | ++ | ++ | ++ |

| | |
|---|---|
| +++ | All cells are positive |
| ++ | +/– 50% of the cells are positive |
| + | +/– 10% of the cells are positive |
| BVDV | Bovine viral diarrhea virus |
| BDV | Border disease virus |
| cp | Cytopathogen strain |
| ncp | Non cytopathogen strain |

Especially against BVDVI cp, the BVDV strain which resembles HCV most, the effect of artemether can be seen clearly. The product has an $EC_{90}$=0.16 µg/ml. The toxic concentration in these experiments was found to be around 100 µg/ml. Also against BDV, an effect could be observed ($EC_{90}$=0.8 µg/ml).

Artemisinin and the crude *Artemisia* extracts (KE-4, KE-5 and KE-6) were screened against the tumor cell lines L1210/0, FM3A/0, Molt4/C8 and CEM/0, but no interesting activity could be found.

CONCLUSION

In the first screenings against DNA-viruses and retroviruses we could not notice any significant antiviral activity. In the second screenings against the BVDV (RNA virus) we clearly indicated strong anti-viral activity of artemisinin, artesunate, artemether, and dihydroartemisinin. These products, all endoperoxides, showed significant better activity against BVDV, compared to the tested crude Artemisia extracts. Since BVDV and HCV have many similarities, artemisinin, artemether, artesunate, dihydroartemisinin and probably other peroxides may have strong and selective antiviral properties against HCV.

Although the invention has been described with respect to a preferred embodiment thereof, it is to be also understood that it is not to be so limited since changes and modifications can be made therein which are within the full intended scope of this invention as defined by the appended claims.

We claim:

1. A method of treating an infection caused by *Flaviviridae* sp., comprising the step of administering an effective amount of a sesquiterpene having the formula:

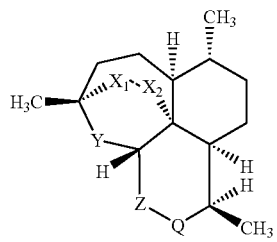

wherein:
  $X_1$ and $X_2$ are O;
  Y is O;
  Z is O, and
  Q is selected from the group consisting of CO, CHOH, $CHOCH_3$, $CHOC_2H_5$, $CHOC_3H_7$, and $CHOCOCCH_2CH_2COOH$,
and the pharmaceutically acceptable salts thereof; and wherein the infection is hepatitis C or bovine viral diarrhea.

2. The method as defined in claim 1, wherein the infection is hepatitis C.

3. The method according to claim 2, wherein the sesquiterpene is administered in combination with interferon or peg-interferon.

* * * * *